(12) United States Patent
Bruinzeel et al.

(10) Patent No.: US 8,637,464 B2
(45) Date of Patent: Jan. 28, 2014

(54) P75$^{NTR}$ SCREENING ASSAY

(75) Inventors: Wouter David Bruinzeel, Breda (NL); Miroslav Cik, Boechout (BE)

(73) Assignee: Janssen Pharmaceutica N.V., Beerse (BE)

( * ) Notice: Subject to any disclaimer, the term of this patent is extended or adjusted under 35 U.S.C. 154(b) by 664 days.

(21) Appl. No.: 11/632,395

(22) PCT Filed: Jul. 11, 2005

(86) PCT No.: PCT/EP2005/053304
§ 371 (c)(1),
(2), (4) Date: Jan. 11, 2007

(87) PCT Pub. No.: WO2006/005740
PCT Pub. Date: Jan. 19, 2006

(65) Prior Publication Data
US 2008/0064036 A1    Mar. 13, 2008

Related U.S. Application Data

(60) Provisional application No. 60/588,551, filed on Jul. 16, 2004.

(30) Foreign Application Priority Data

Jul. 14, 2004 (EP) ..................... 04103368

(51) Int. Cl.
*A61K 38/57* (2006.01)
*C12P 21/06* (2006.01)
*C12N 15/74* (2006.01)
*C12N 5/02* (2006.01)
*G01N 33/48* (2006.01)

(52) U.S. Cl.
USPC ..... 514/18.9; 435/7.95; 435/69.1; 435/320.1; 435/325; 435/383; 702/21

(58) Field of Classification Search
None
See application file for complete search history.

(56) References Cited

U.S. PATENT DOCUMENTS

| | | | |
|---|---|---|---|
| 5,834,196 A | * | 11/1998 | Reutelingsperger ............... 435/6 |
| 6,713,261 B1 | | 3/2004 | Pallardy et al. |
| 2002/0137188 A1 | | 9/2002 | Bartlett et al. |

FOREIGN PATENT DOCUMENTS

WO    WO 01/52843 A1    7/2001

OTHER PUBLICATIONS

Feng et al., In Vitro Cell. Dev. Biol., 39:420-423, Nov.-Dec. 2003.*
HomoloGene report: NGFR (p75NTR). Retrieved online from: <http://www.ncbi.nlm.nih.gov/sites/homologene/1877> Retrieved on: Mar. 8, 2010.*
Chen et al., CNS & Neurological Disorders—Drug Targets, 7(6): 512-523, 2008.*
Chu et al., Current Opinion in Biotech., 12(2):180-187, 2001.*
UniProt Accession No. P08138, TNR16_Human, integrated Aug. 1988 (view in Score).*
UniProt Accession No. Q9Z0W1, TNR16_Mouse, May 2002 (view in Score).*
Coulson et al., "Chopper, a New Death Domain of the p75 Neurotrophin Receptor That Mediates Rapid Neuronal Cell Death", The Journal of Biological Chemistry, vol. 275, No. 39, pp. 30537-30545 (2000).
Tabassum et al., "The p75$^{NTH}$ Tumor Suppression Induces Caspase-Mediated Apoptosis in Bladder Tumor Cells", Int. J. Cancer, vol. 105, pp. 47-52 (2003).
Bhakar et al., "Apoptosis Induced by p75NTR Overexpression Requires Jun Kinase-Dependent Phosphorylation of Bad", The Journal of Neuroscience, vol. 23, No. 36, pp. 11373-11381 (2003).
Kanning et al., "Proteolytic Processing of the p75 Neurotrophin Receptor and Two Homologs Generates C-Terminal Fragments with Signaling Capability", The Journal of Neuroscience, vol. 23, No. 13, pp. 5425-5436 (2003).
International Search Report dated Mar. 21, 2006 for related International Application No. PCT/EP2005/053304.

* cited by examiner

*Primary Examiner* — Daniel E Kolker
*Assistant Examiner* — Stacey N MacFarlane

(57) ABSTRACT

The present invention provides a method to identify a test compounds capability to modulate p75.sup.NTR induced apoptosis, said method comprising: i. Transfecting a suspension of eukaryotic cells with a vector encoding SEQ ID No.4 OR SEQ ID No.6), ii. Contacting said cells with the compound to be tested, and iii. Determine the apoptotic response in said cells, wherein an alteration in apoptotic response in the presence of said test compound compared to the apoptotic response in the absence of the test compound is an indication of the ability of the test compound to modulate p75.sup.NTR induced apoptosis.

12 Claims, 1 Drawing Sheet

SEQUENCE LISTING

<160> NUMBER OF SEQ ID NOS: 13

<210> SEQ ID NO 1
<211> LENGTH: 1604
<212> TYPE: DNA
<213> ORGANISM: Rattus norvegicus

<400> SEQUENCE: 1

```
aattcccggg gatccgtcga cctgcagggg ggggggggc agctccggcg ggcagcaggc      60
gctggagcgc atcgcagttc agctcagcgc agcaccatcg gtctgcggag cggactgagc     120
tagaagcgga gcgctgacgc cggaggcgtg caatgaggag ggcaggtgct gcctgcagcg     180
ccatggaccg gctgcgcctg ctgctgctgc tgattctagg ggtgtcctct ggaggtgcca     240
aggagacatg ttccacaggc ctgtacaccc acagcggaga gtgctgcaaa gcctgcaact     300
tgggcgaagg cgtggcccag ccctgcggag ccaaccagac cgtgtgtgaa ccctgcctgg     360
acaatgttac attctccgat gtggtgagcg ccactgagcc gtgcaagccg tgcaccgagt     420
gcctgggcct gcagagcatg tccgctccct gtgtggaggc agacgatgca gtgtgcagat     480
gtgcctatgg ctactaccag gacgaggaga ctggccactg tgaggcttgc agcgtgtgcg     540
aggtgggctc gggactcgtg ttctcctgcc aggacaaaca gaacacagtg tgtgaagagt     600
gcccagaggg cacatactca gacgaagcca accacgtgga cccgtgccta ccctgcacgg     660
tgtgcgagga cactgagcgc cagttacgcg agtgcacgcc ctgggctgat gctgaatgcg     720
aagagatccc tggtcgatgg atcccaaggt ctacgccccc ggagggctcc gacagcacag     780
cgcccagcac ccaggagcct gaggttcctc cagagcaaga ccttgtaccc agtacagtgg     840
cggatatggt gaccactgtg atgggcagct cccagcctgt agtgacccgc ggcaccaccg     900
acaacctcat tcctgtctat tgctccatct tggctgctgt ggtcgtgggc cttgtggcct     960
atattgcttt caagaggtgg aacagctgca aacaaaataa acaaggcgcc aacagccgcc    1020
ccgtgaacca gacgccccca ccggagggag agaaactgca cagcgacagt ggcatctctg    1080
tggacagcca gagcctgcac gaccagcaga cccatacgca gactgcctca ggccaggccc    1140
tcaagggtga tggcaacctc tacagtagcc tgccctgac caagcgtgag gaggtagaga    1200
aactgctcaa cggggatacc tggcgacatc tggcaggcga gctgggttac cagcctgaac    1260
atatagactc ctttacccac gaggcctgcc cagtgcgagc cctgctggcc agctggggtg    1320
cccaggacag tgcaacgctt gatgcccttt agccgccct gcgacgcatc cagagagctg    1380
acattgtgga gagtctatgc agcgagtcca ctgccacatc cccagtgtga actcacagac    1440
tgggagcccc tgtcctgtcc cacattccga cgactgatgt tctagccagc ccccacagag    1500
ctgccccctc tccctcgggg atggcccaac ggtcagaacg gagcatctct gtgcagggcc    1560
tctgtgttcc cactcctgac tccgttgctg ctcccgaggg ggcc                     1604
```

<210> SEQ ID NO 2
<211> LENGTH: 425
<212> TYPE: PRT
<213> ORGANISM: Rattus norvegicus

<400> SEQUENCE: 2

Met Arg Arg Ala Gly Ala Ala Cys Ser Ala Met Asp Arg Leu Arg Leu
1               5                   10                  15

Leu Leu Leu Leu Ile Leu Gly Val Ser Ser Gly Gly Ala Lys Glu Thr
            20                  25                  30

-continued

Cys Ser Thr Gly Leu Tyr Thr His Ser Gly Glu Cys Cys Lys Ala Cys
     35                      40                     45

Asn Leu Gly Glu Gly Val Ala Gln Pro Cys Gly Ala Asn Gln Thr Val
 50                         55                      60

Cys Glu Pro Cys Leu Asp Asn Val Thr Phe Ser Asp Val Val Ser Ala
65                    70                    75                80

Thr Glu Pro Cys Lys Pro Cys Thr Glu Cys Leu Gly Leu Gln Ser Met
             85                      90                    95

Ser Ala Pro Cys Val Glu Ala Asp Asp Ala Val Cys Arg Cys Ala Tyr
          100                  105                110

Gly Tyr Tyr Gln Asp Glu Glu Thr Gly His Cys Glu Ala Cys Ser Val
     115                  120                125

Cys Glu Val Gly Ser Gly Leu Val Phe Ser Cys Gln Asp Lys Gln Asn
     130                  135                140

Thr Val Cys Glu Glu Cys Pro Glu Gly Thr Tyr Ser Asp Glu Ala Asn
145                   150                   155              160

His Val Asp Pro Cys Leu Pro Cys Thr Val Cys Glu Asp Thr Glu Arg
          165                  170                175

Gln Leu Arg Glu Cys Thr Pro Trp Ala Asp Ala Glu Cys Glu Glu Ile
     180                  185                190

Pro Gly Arg Trp Ile Pro Arg Ser Thr Pro Pro Glu Gly Ser Asp Ser
     195                  200                205

Thr Ala Pro Ser Thr Gln Glu Pro Glu Val Pro Pro Glu Gln Asp Leu
     210                  215                220

Val Pro Ser Thr Val Ala Asp Met Val Thr Thr Val Met Gly Ser Ser
225                   230                   235              240

Gln Pro Val Val Thr Arg Gly Thr Thr Asp Asn Leu Ile Pro Val Tyr
          245                  250                255

Cys Ser Ile Leu Ala Ala Val Val Val Gly Leu Val Ala Tyr Ile Ala
          260                  265                270

Phe Lys Arg Trp Asn Ser Cys Lys Gln Asn Lys Gln Gly Ala Asn Ser
     275                  280                285

Arg Pro Val Asn Gln Thr Pro Pro Glu Gly Glu Lys Leu His Ser
     290                  295                300

Asp Ser Gly Ile Ser Val Asp Ser Gln Ser Leu His Asp Gln Thr
305                   310                   315              320

His Thr Gln Thr Ala Ser Gly Gln Ala Leu Lys Gly Asp Gly Asn Leu
          325                  330                335

Tyr Ser Ser Leu Pro Leu Thr Lys Arg Glu Glu Val Glu Lys Leu Leu
          340                  345                350

Asn Gly Asp Thr Trp Arg His Leu Ala Gly Glu Leu Gly Tyr Gln Pro
     355                  360                365

Glu His Ile Asp Ser Phe Thr His Glu Ala Cys Pro Val Arg Ala Leu
     370                  375                380

Leu Ala Ser Trp Gly Ala Gln Asp Ser Ala Thr Leu Asp Ala Leu Leu
385                   390                   395              400

Ala Ala Leu Arg Arg Ile Gln Arg Ala Asp Ile Val Glu Ser Leu Cys
          405                  410                415

Ser Glu Ser Thr Ala Thr Ser Pro Val
          420                  425

<210> SEQ ID NO 3
<211> LENGTH: 930
<212> TYPE: DNA
<213> ORGANISM: rattus norvegicus

<400> SEQUENCE: 3

```
gaattccagc tccggcgggc agcaggcgct ggagcgcatc gcagttcagc tcagcgcagc    60
accatcggtc tgcggagcgg actgagctag aagcggagcg ctgacgccgg aggcgtgcaa   120
tgaggagggc aggtgctgcc tgcagcgcca tggaccggct gcgcctgctg ctgctgctga   180
ttctaggggt gtcctctgga ggtgccaagg agacaggcac caccgacaac ctcattcctg   240
tctattgctc catcttggct gctgtggtcg tgggccttgt ggcctatatt gctttcaaga   300
ggtggaacag ctgcaaacaa ataaacaag gcgccaacag ccgccccgtg aaccagacgc    360
ccccaccgga gggagagaaa ctgcacagcg acagtggcat ctctgtggac agccagagcc   420
tgcacgacca gcagacccat acgcagactg cctcaggcca ggccctcaag ggtgatggca   480
acctctacag tagcctgccc ctgaccaagc gtgaggaggt agagaaactg ctcaacgggg   540
atacctggcg acatctggca ggcgagctgg gttaccagcc tgaacatata gactccttta   600
cccacgaggc ctgcccagtg cgagccctgc tggccagctg gggtgccag acagtgcaa    660
cgcttgatgc cctttagcc gccctgcgac gcatccagag agctgacatt gtggagagtc   720
tatgcagcga gtccactgcc acatccccag tgtgaactca cagactggga gccctgtcc   780
tgtcccacat tccgacgact gatgttctag ccagccccca cagagctgcc cctctccct   840
cggggatggc ccaacggtca gaacggagca tctctgtgca gggcctctgt gttcccactc   900
ctgactccgt tgctgctccc gagggggccc                                   930
```

<210> SEQ ID NO 4
<211> LENGTH: 211
<212> TYPE: PRT
<213> ORGANISM: rattus norvegicus

<400> SEQUENCE: 4

```
Met Arg Arg Ala Gly Ala Ala Cys Ser Ala Met Asp Arg Leu Arg Leu
1               5                   10                  15

Leu Leu Leu Leu Ile Leu Gly Val Ser Ser Gly Gly Ala Lys Glu Thr
            20                  25                  30

Gly Thr Thr Asp Asn Leu Ile Pro Val Tyr Cys Ser Ile Leu Ala Ala
        35                  40                  45

Val Val Val Gly Leu Val Ala Tyr Ile Ala Phe Lys Arg Trp Asn Ser
    50                  55                  60

Cys Lys Gln Asn Lys Gln Gly Ala Asn Ser Arg Pro Val Asn Gln Thr
65                  70                  75                  80

Pro Pro Pro Glu Gly Glu Lys Leu His Ser Asp Ser Gly Ile Ser Val
                85                  90                  95

Asp Ser Gln Ser Leu His Asp Gln Gln Thr His Thr Gln Thr Ala Ser
            100                 105                 110

Gly Gln Ala Leu Lys Gly Asp Gly Asn Leu Tyr Ser Ser Leu Pro Leu
        115                 120                 125

Thr Lys Arg Glu Glu Val Glu Lys Leu Leu Asn Gly Asp Thr Trp Arg
    130                 135                 140

His Leu Ala Gly Glu Leu Gly Tyr Gln Pro Glu His Ile Asp Ser Phe
145                 150                 155                 160

Thr His Glu Ala Cys Pro Val Arg Ala Leu Leu Ala Ser Trp Gly Ala
                165                 170                 175

Gln Asp Ser Ala Thr Leu Asp Ala Leu Leu Ala Ala Leu Arg Arg Ile
            180                 185                 190

Gln Arg Ala Asp Ile Val Glu Ser Leu Cys Ser Glu Ser Thr Ala Thr
```

```
                195                 200                 205
Ser Pro Val
    210
```

<210> SEQ ID NO 5
<211> LENGTH: 577
<212> TYPE: DNA
<213> ORGANISM: rattus norvegicus

<400> SEQUENCE: 5

```
aattccagct ccggcgggca gcaggcgctg gagcgcatcg cagttcagct cagcgcagca     60
ccatcggtct gcggagcgga ctgagctaga agcggagcgc tgacgccgga ggcgtgcaat    120
gaggagggca ggtgctgcct gcagcgccat ggaccggctg cgcctgctgc tgctgctgat    180
tctagggtg tcctctggag gtgccaagga gacaggcacc accgacaacc tcattcctgt    240
ctattgctcc atcttggctg ctgtggtcgt gggccttgtg gcctatattg ctttcaagag    300
gtggaacagc tgcaaacaaa ataaacaagg cgccaacagc cgccccgtga accagacgcc    360
cccaccggag ggagagaaac tgcacagcga cagtggcatc tgaactcaca gactgggagc    420
ccctgtcctg tcccacattc cgacgactga tgttctagcc agcccccaca gagctgcccc    480
ctctccctcg gggatggccc aacggtcaga acggagcatc tctgtgcagg gcctctgtgt    540
tcccactcct gactccgttg ctgctcccga gggggcc                             577
```

<210> SEQ ID NO 6
<211> LENGTH: 94
<212> TYPE: PRT
<213> ORGANISM: rattus norvegicus

<400> SEQUENCE: 6

```
Met Arg Arg Ala Gly Ala Ala Cys Ser Ala Met Asp Arg Leu Arg Leu
1               5                   10                  15
Leu Leu Leu Leu Ile Leu Gly Val Ser Ser Gly Gly Ala Lys Glu Thr
            20                  25                  30
Gly Thr Thr Asp Asn Leu Ile Pro Val Tyr Cys Ser Ile Leu Ala Ala
        35                  40                  45
Val Val Val Gly Leu Val Ala Tyr Ile Ala Phe Lys Arg Trp Asn Ser
    50                  55                  60
Cys Lys Gln Asn Lys Gln Gly Ala Asn Ser Arg Pro Val Asn Gln Thr
65                  70                  75                  80
Pro Pro Pro Glu Gly Glu Lys Leu His Ser Asp Ser Gly Ile
            85                  90
```

<210> SEQ ID NO 7
<211> LENGTH: 871
<212> TYPE: DNA
<213> ORGANISM: rattus norvegicus

<400> SEQUENCE: 7

```
gaattccagc tccggcgggc agcaggcgct ggagcgcatc gcagttcagc tcagcgcagc     60
accatcggtc tgcggagcgg actgagctag aagcggagcg ctgacgccgg aggcgtgcaa    120
tgaggagggc aggtgctgcc tgcagcgcca tggaccggct gcgcctgctg ctgctgctga    180
ttctaggggt gtcctctgga ggtgccaagg agacataccc atacgacgtc ccagactacg    240
ctggcaccac cgacaacctc attcctgtct attgctccat cttggctgct gtggtcgtgg    300
gccttgtggc ctatattgct ttccacacgc acagtgcat ctctgtggac agccagagcc    360
tgcacgacca gcagacccat acgcagactg cctcaggcca ggccctcaag ggtgatggca    420
```

```
acctctacag tagcctgccc ctgaccaagc gtgaggaggt agagaaactg ctcaacgggg    480
atacctggcg acatctggca ggcgagctgg gttaccagcc tgaacatata gactccttta    540
cccacgaggc ctgcccagtg cgagccctgc tggccagctg gggtgcccag gacagtgcaa    600
cgcttgatgc cctttagcc gccctgcgac gcatccagag agctgacatt gtggagagtc    660
tatgcagcga gtccactgcc acatcccag tgtgaactca cagactggga gcccctgtcc    720
tgtcccacat tccgacgact gatgttctag ccagccccca cagagctgcc ccctctccct    780
cggggatggc ccaacggtca gaacggagca tctctgtgca gggcctctgt gttcccactc    840
ctgactccgt tgctgctccc gagggggccc t    871

<210> SEQ ID NO 8
<211> LENGTH: 191
<212> TYPE: PRT
<213> ORGANISM: Rattus norvegicus

<400> SEQUENCE: 8

Met Arg Arg Ala Gly Ala Ala Cys Ser Ala Met Asp Arg Leu Arg Leu
1               5                   10                  15

Leu Leu Leu Leu Ile Leu Gly Val Ser Ser Gly Gly Ala Lys Glu Thr
            20                  25                  30

Tyr Pro Tyr Asp Val Pro Asp Tyr Ala Gly Thr Thr Asp Asn Leu Ile
        35                  40                  45

Pro Val Tyr Cys Ser Ile Leu Ala Ala Val Val Gly Leu Val Ala
    50                  55                  60

Tyr Ile Ala Phe His Ser Asp Ser Gly Ile Ser Val Asp Ser Gln Ser
65                  70                  75                  80

Leu His Asp Gln Gln Thr His Thr Gln Thr Ala Ser Gly Gln Ala Leu
                85                  90                  95

Lys Gly Asp Gly Asn Leu Tyr Ser Ser Leu Pro Leu Thr Lys Arg Glu
            100                 105                 110

Glu Val Glu Lys Leu Leu Asn Gly Asp Thr Trp Arg His Leu Ala Gly
        115                 120                 125

Glu Leu Gly Tyr Gln Pro Glu His Ile Asp Ser Phe Thr His Glu Ala
    130                 135                 140

Cys Pro Val Arg Ala Leu Leu Ala Ser Trp Gly Ala Gln Asp Ser Ala
145                 150                 155                 160

Thr Leu Asp Ala Leu Leu Ala Ala Leu Arg Arg Ile Gln Arg Ala Asp
                165                 170                 175

Ile Val Glu Ser Leu Cys Ser Glu Ser Thr Ala Thr Ser Pro Val
            180                 185                 190

<210> SEQ ID NO 9
<211> LENGTH: 87
<212> TYPE: DNA
<213> ORGANISM: Rattus norvegicus

<400> SEQUENCE: 9
aagaggtgga acagctgcaa acaaaataaa caaggcgcca acagccgccc cgtgaaccag    60
acgcccccac cggagggaga gaaactg    87

<210> SEQ ID NO 10
<211> LENGTH: 29
<212> TYPE: PRT
<213> ORGANISM: Rattus norvegicus

<400> SEQUENCE: 10
```

Lys Arg Trp Asn Ser Cys Lys Gln Asn Lys Gln Gly Ala Asn Ser Arg
1               5                   10                  15

Pro Val Asn Gln Thr Pro Pro Glu Gly Glu Lys Leu
            20                  25

<210> SEQ ID NO 11
<211> LENGTH: 427
<212> TYPE: PRT
<213> ORGANISM: homo sapiens

<400> SEQUENCE: 11

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
            20                  25                  30

Pro Thr Gly Leu Tyr Thr His Ser Gly Glu Cys Cys Lys Ala Cys Asn
        35                  40                  45

Leu Gly Glu Gly Val Ala Gln Pro Cys Gly Ala Asn Gln Thr Val Cys
    50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
        115                 120                 125

Glu Ala Gly Ser Gly Leu Val Phe Ser Cys Gln Asp Lys Gln Asn Thr
    130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
        195                 200                 205

Ala Pro Ser Thr Gln Glu Pro Glu Ala Pro Pro Glu Gln Asp Leu Ile
    210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Val Gly Leu Val Ala Tyr Ile Ala Phe
            260                 265                 270

Lys Arg Trp Asn Ser Cys Lys Gln Asn Lys Gln Gly Ala Asn Ser Arg
        275                 280                 285

Pro Val Asn Gln Thr Pro Pro Glu Gly Glu Lys Leu His Ser Asp
    290                 295                 300

Ser Gly Ile Ser Val Asp Ser Gln Ser Leu His Asp Gln Gln Pro His
305                 310                 315                 320

Thr Gln Thr Ala Ser Gly Gln Ala Leu Lys Gly Asp Gly Gly Leu Tyr
                325                 330                 335

Ser Ser Leu Pro Pro Ala Lys Arg Glu Glu Val Glu Lys Leu Leu Asn
            340                 345                 350

-continued

Gly Ser Ala Gly Asp Thr Trp Arg His Leu Ala Gly Glu Leu Gly Tyr
            355                 360                 365

Gln Pro Glu His Ile Asp Ser Phe Thr His Glu Ala Cys Pro Val Arg
        370                 375                 380

Ala Leu Leu Ala Ser Trp Ala Thr Gln Asp Ser Ala Thr Leu Asp Ala
385                 390                 395                 400

Leu Leu Ala Ala Leu Arg Arg Ile Gln Arg Ala Asp Leu Val Glu Ser
                405                 410                 415

Leu Cys Ser Glu Ser Thr Ala Thr Ser Pro Val
                420                 425

<210> SEQ ID NO 12
<211> LENGTH: 417
<212> TYPE: PRT
<213> ORGANISM: mus musculus

<400> SEQUENCE: 12

Met Asp Arg Leu Arg Leu Leu Leu Leu Leu Leu Leu Leu Leu Gly Val
1               5                   10                  15

Ser Phe Gly Gly Ala Lys Glu Thr Cys Ser Thr Gly Met Tyr Thr His
            20                  25                  30

Ser Gly Glu Cys Cys Lys Ala Cys Asn Leu Gly Glu Gly Val Ala Gln
        35                  40                  45

Pro Cys Gly Ala Asn Gln Thr Val Cys Glu Pro Cys Leu Asp Ser Val
    50                  55                  60

Thr Phe Ser Asp Val Val Ser Ala Thr Glu Pro Cys Lys Pro Cys Thr
65                  70                  75                  80

Glu Cys Leu Gly Leu Gln Ser Met Ser Ala Pro Cys Val Glu Ala Asp
                85                  90                  95

Asp Ala Val Cys Arg Cys Ser Tyr Gly Tyr Tyr Gln Asp Glu Glu Thr
            100                 105                 110

Gly Arg Cys Glu Ala Cys Ser Val Cys Gly Val Gly Ser Gly Leu Val
        115                 120                 125

Phe Ser Cys Gln Asp Lys Gln Asn Thr Val Cys Glu Glu Cys Pro Glu
    130                 135                 140

Gly Thr Tyr Ser Asp Glu Ala Asn His Val Asp Pro Cys Leu Pro Cys
145                 150                 155                 160

Thr Val Cys Glu Asp Thr Glu Arg Gln Leu Arg Glu Cys Thr Pro Trp
                165                 170                 175

Ala Asp Ala Glu Cys Glu Glu Ile Pro Gly Arg Trp Ile Thr Arg Ser
            180                 185                 190

Thr Pro Pro Glu Gly Ser Asp Val Thr Thr Pro Ser Thr Gln Glu Pro
        195                 200                 205

Glu Ala Pro Pro Glu Arg Asp Leu Ile Ala Ser Thr Val Ala Asp Thr
    210                 215                 220

Val Thr Thr Val Met Gly Ser Ser Gln Pro Val Val Thr Arg Gly Thr
225                 230                 235                 240

Ala Asp Asn Leu Ile Pro Val Tyr Cys Ser Ile Leu Ala Ala Val Val
                245                 250                 255

Val Gly Leu Val Ala Tyr Ile Ala Phe Lys Arg Trp Asn Ser Cys Lys
            260                 265                 270

Gln Asn Lys Gln Gly Ala Asn Ser Arg Pro Val Asn Gln Thr Pro Pro
        275                 280                 285

Pro Glu Gly Glu Lys Leu His Ser Asp Ser Gly Ile Ser Val Asp Ser
    290                 295                 300

```
Gln Ser Leu His Asp Gln Gln Thr His Thr Gln Thr Ala Ser Ala Gln
305                 310                 315                 320

Ala Leu Lys Gly Asp Gly Asn Leu Tyr Ser Ser Leu Pro Leu Thr Lys
            325                 330                 335

Arg Glu Glu Val Glu Lys Leu Leu Asn Gly Asp Thr Trp Arg His Leu
            340                 345                 350

Ala Gly Glu Leu Gly Tyr Gln Pro Glu His Ile Asp Ser Phe Thr His
            355                 360                 365

Glu Ala Cys Pro Val Arg Ala Leu Leu Ala Ser Trp Gly Ala Gln Asp
        370                 375                 380

Ser Ala Thr Leu Asp Ala Leu Leu Ala Ala Leu Arg Arg Ile Gln Arg
385                 390                 395                 400

Ala Asp Ile Val Glu Ser Leu Cys Ser Glu Ser Thr Ala Thr Ser Pro
                405                 410                 415

Val

<210> SEQ ID NO 13
<211> LENGTH: 416
<212> TYPE: PRT
<213> ORGANISM: gallus gallus

<400> SEQUENCE: 13

Met Ala Gly Phe Val Pro Leu Leu Leu Leu Leu Pro Ala Gly Pro
1               5                   10                  15

Thr Trp Gly Ser Lys Glu Lys Cys Leu Thr Lys Met Tyr Thr Thr Ser
            20                  25                  30

Gly Glu Cys Cys Lys Ala Cys Asn Leu Gly Glu Gly Val Val Gln Pro
        35                  40                  45

Cys Gly Val Asn Gln Thr Val Cys Glu Pro Cys Leu Asp Ser Val Thr
    50                  55                  60

Tyr Ser Asp Thr Val Ser Ala Thr Glu Pro Cys Lys Pro Cys Thr Gln
65                  70                  75                  80

Cys Val Gly Leu His Ser Met Ser Ala Pro Cys Val Glu Ser Asp Asp
                85                  90                  95

Ala Val Cys Arg Cys Ala Tyr Gly Tyr Phe Gln Asp Glu Leu Ser Gly
            100                 105                 110

Ser Cys Lys Glu Cys Ser Ile Cys Glu Val Gly Phe Gly Leu Met Phe
        115                 120                 125

Pro Cys Arg Asp Ser Gln Asp Thr Val Cys Glu Glu Cys Pro Glu Gly
    130                 135                 140

Thr Phe Ser Asp Glu Ala Asn Phe Val Asp Pro Cys Leu Pro Cys Thr
145                 150                 155                 160

Ile Cys Glu Glu Asn Glu Val Met Val Lys Glu Cys Thr Ala Thr Ser
                165                 170                 175

Asp Ala Glu Cys Arg Asp Leu His Pro Arg Trp Thr Thr His Thr Pro
            180                 185                 190

Ser Leu Ala Gly Ser Asp Ser Pro Glu Pro Ile Thr Arg Asp Pro Phe
        195                 200                 205

Asn Thr Glu Gly Met Ala Thr Thr Leu Ala Asp Ile Val Thr Thr Val
    210                 215                 220

Met Gly Ser Ser Gln Pro Val Val Ser Arg Gly Thr Ala Asp Asn Leu
225                 230                 235                 240

Ile Pro Val Tyr Cys Ser Ile Leu Ala Ala Val Val Val Gly Leu Val
                245                 250                 255
```

```
Ala Tyr Ile Ala Phe Lys Arg Trp Asn Ser Cys Lys Gln Asn Lys Gln
            260             265             270

Gly Ala Asn Asn Arg Pro Val Asn Gln Thr Pro Ser Pro Glu Gly Glu
        275             280             285

Lys Leu His Ser Asp Ser Gly Ile Ser Val Asp Ser Gln Ser Leu His
        290             295             300

Asp Gln Gln Pro Pro Asn Gln Ser Thr Gln Gly Pro Ala Pro Lys Gly
305             310             315             320

Asp Gly Ser Leu Tyr Ala Ser Leu Pro Pro Ser Lys Gln Glu Glu Val
            325             330             335

Glu Lys Leu Leu Ser Ser Ser Ala Glu Glu Thr Trp Arg Gln Leu Ala
            340             345             350

Gly Glu Leu Gly Tyr Lys Glu Asp Leu Ile Asp Cys Phe Thr Arg Glu
        355             360             365

Glu Ser Pro Ala Arg Ala Leu Leu Ala Asp Trp Ser Ala Lys Glu Thr
    370             375             380

Ala Thr Leu Asp Ala Leu Leu Val Ala Leu Arg Lys Ile Gln Arg Gly
385             390             395             400

Asp Ile Ala Glu Ser Leu Tyr Ser Glu Ser Thr Ala Thr Ser Pro Val
            405             410             415
```

P75$^{NTR}$ SCREENING ASSAY

CROSS REFERENCE TO RELATED APPLICATIONS

This application is the U.S. national stage of Application No. PCT/EP2005/053304, filed Jul. 11, 2005, which application claims priority from EP patent application 04103368.9, filed Jul. 14, 2002 and U.S. Provisional Application No. 60/588,551, filed Jul. 16, 2004, the entire disclosures of which are hereby incorporated in their entirety.

The present invention relates to the field of apoptotic screening methods and provides assays and kits for the screening of test compounds for their capability to prevent apoptosis in a subject, in particular to prevent apoptosis in case of neurodegenerative disorders. Said assays and kits are based on the finding that the simultaneous measurement of an apoptotic marker and cell death in cell suspensions transfected with p75 neurotrophin receptor or a neuronal death inducing fragment thereof can be exploited to predict potential of compounds in the prevention of neuronal death and accordingly useful in the treatment of neurodegenerative disorders The present invention finds particularly advantageous use in high throughput screening of chemical compound libraries.

BACKGROUND OF THE INVENTION

The p75 neurotrophin receptor (p75$^{NTR}$), a member of the tumor necrosis factor receptor (TNRF) family, is a 75 kDa cell-surface receptor glycoprotein that binds with similar affinity to the neurotrophin family (brain-derived neurotrophic factor, neurotrophin-3 and neurotrophin-4/5) of growth factors. It was the first receptor described for nerve growth factor (NGF) and shown to facilitate Tyrosine kinase receptor (Trk) signal transduction by the formation of high affinity neurotrophin receptor complexes. In contrast to p75$^{NTR}$ the Trk receptor family binds the neurotrophins with varying specificity resulting in cell survival and process outgrowth.

Although providing a definitive function for p75$^{NTR}$ signalling remains controversial, there is substantial evidence to support the hypothesis that p75$^{NTR}$ can initiate a caspase-mediated, i.e mitochondria-mediated apoptotic pathway in a variety of neural and non-neural cell types. A possible role as a tumor and a metastasis suppressor in tumor cells was recently shown in the capability of p75$^{NTR}$ to suppress growth and nerve growth-factor mediated metastasis of human prostate cancer cells and in the effect of p75$^{NTR}$ expression on the cell survival, proliferation and growth of the human cancer cell line T24. Evidence to support a role for p75$^{NTR}$ as a neuronal death inducing factor is based on experiments wherein an increased cell death upon treatment of various neural cell types such as for example developing chick retinas or cultured sympathetic neurons and proprioceptive neurons with brain-derived neurotrophic factor and/or NGF, can be prevented by application of p75$^{NTR}$ antibodies.

p75$^{NTR}$ has sequence similarity to other TNRF family members both in the cysteine-rich extodomain and in the cytoplasmic sequence known as the death domain. Despite the presence of a death domain in p75$^{NTR}$ there is accumulating evidence that this region does not mediate the ability of p75$^{NTR}$ to promote cell death. Unlike the TNRF death domain the death domain of p75$^{NTR}$ does not interact with other death-domain containing proteins, does not spontaneously multimerize in solution and does not function in the same manner. In fact, it was recently shown that deletion of the death domain sequence has no effect on the ability of p75$^{NTR}$ to kill. Instead of the death domain, the cytoplasmic juxtamembrane region of the p75$^{NTR}$ has been found to be necessary and sufficient to initiate neural cell death. The region was named "Chopper" and shown to induce apoptotic cell death only when bound to the plasma membrane by a lipid anchor.

Apoptosis or programmed cell death is a physiological mechanism to eliminate cells in different tissues during embryogenesis, morphogenesis and cell renewal. Apoptosis is a genetically controlled mechanism that intervenes at advanced and irreversible stages of cell damage. It is accordingly established that apoptosis plays a key role in neuronal death that occurs in some of the major disorders of the CNS such as stroke, Parkinson's disease, Huntington's disease, Alzheimer's disease, Amyotrophic lateral sclerosis (ALS), epilepsy, Spinal Cord Injury (SCI), Multiple Sclerosis (MS), Motor Neuron Disease (MND) and other neurodegenerative diseases (Park et al. 2000; Oh et al. 2000; Lowry et al. 2001; Sedel et al. 1999; Dowling et al. 1999).

In addition to the above, numerous studies show an increased expression of p75$^{NTR}$ after ishemia in brain and heart regions where an massive apoptosis was enregistered. These results suggest that p75$^{NTR}$ may play an important role in neuronal death by post-ischemic apoptosis (Park et al, J. Neuroscience, 2000, 20, 9096-9103).

The p75$^{NTR}$ receptor is also described as cellular signalling partner for Prion and β-amyloid peptides (Della-Bianca et al., J. Biol. Chem. 2001, 276, 38929-38933) and is accordingly involved in the neurotoxic action of these components. These results support the hypothesis that p75$^{NTR}$ would play an important role in the neuronal death observed in prion diseases, i.e. Transmissible spongiform encephalopathies (TSE) and Alzheimer's disease.

Recent studies provide a role for the p75$^{NTR}$ receptor as coreceptor in the signalling pathway of the myelin inhibitory components, i.e. myelin-associated glycoprotein (MAG), Nogo and oligodendrocyte-myelin glycoprotein (Omgp). All of these proteins are localised in the membrane of oligodendrocytes immediately adjacent to the axone and inhibit neuronal growth by binding a common receptor, the Nogo66 receptor (NgR). NgR is linked to the cell surface by means of a glycosylphosphatidylinositol (GPI) anchor but lacks an intracellular signalling domain and accordingly needs p75$^{NTR}$ as signalling partner. It was found that disruption of the NgR signalling complex prevents the inhibitory action of MAG. Hence, as a coreceptor of NgR, p75$^{NTR}$ now emerges as a key player, not only for regulating neuronal development and apoptosis, but also for regulating the inhibition of axon regeneration induced by myelin-associated factors and as such provides a therapeutic target to promote neuronal regeneration.

Although the major role for p75$^{NTR}$ is CNS related, some recent work shows an increased expression of neutrophines and p75$^{NTR}$ with a concomitant apoptosis at lesions caused by atherosclerosis. In addition, for a short variant of p75$^{NTR}$, that arises from alternative splicing of exon III in the p75$^{NTR}$ locus, it was shown in transgenic mice that the absence of p75$^{NTR}$ leads to a severe phenotype, including partial perinatal lethality and defects in the vascular system. An involvement of neurotrophins and Trk receptors in vasculogenesis has previously been demonstrated; all neurotrophins are detected in the forming of tunic media of the aorta from E13 onward. TrkB and TrkC are expressed in the developing aorta with expression patterns reciprocal to that of p75$^{NTR}$, and severe heart malformations have been observed in NT3 and in TrkC mutant mice. It thus seems that neurotrophin receptors, now including p75$^{NTR}$, are essential in the formation of blood vessels. All of these findings suggest a paramount role for p75$^{NTR}$ in vascular pathologies such as for example, atherosclerosis, congenital and rheumatic heart disease, and vascular inflammation Notwithstanding the recognition of p75$^{NTR}$ as an important therapeutic target present screening methods rely on the interaction of p75$^{NTR}$ with its ligand NGF either in a competitive binding assay using cell membrane preparations of p75$^{NTR}$ expressing cells and radiolabeled NGF as described by Weskamp (Neuron, 1991, 6, 649-663) or by measuring the effect of the compounds to be tested on NGF induced apoptosis in p75$^{NTR}$ expressing cells as described by Tabassum (Int. J. Cancer, 2003, 105, 47-52). Neither method provides the possibility to study the effects of test compounds on the p75$^{NTR}$ signal transduction irrespective of the ligand used.

Present in vitro screens to identify compounds that modulate the p75$^{NTR}$ signalling activity are based on the transient transfection of adherent cell cultures of sensory neurons, rat PC12 cells, 293T cells and wild-type Schwann cells, using DNA constructs that encode for p75$^{NTR}$ or truncated forms of p75$^{NTR}$ that retain the capability to induce apoptotic cell death upon induction with NGF or leukemia inhibitory factor (LIF) (see for example Coulson et al., J. Biol. Chem. 2000, 275, 30537-30545).

Current methods of drug discovery generally involve assessing the biological activity of tens or hundreds of thousands of compounds in order to identify a small number of those compounds having a desired activity against a particular target, i.e. High Throughput Screening (HTS). In a typical HTS related screen format, assays are performed in multi-well microplates, such as 96, 384 or 1536 well plates, putting certain constrains to the setup of the assay to be performed including the availability of the source materials. HTS related screens are preferably performed at room temperature with a single measurement for each of the compounds tested in the assay, requiring short cycle times, with a reproducible and reliable output.

The present invention describes the development of a p75$^{NTR}$ signalling assay that can be performed in an HTS screen format and which is based on a particular transfection method applicable to eukaryotic cells such as for example Hek293T cells.

SUMMARY OF THE INVENTION

The present invention provides a method to identify a test compounds capability to modulate p75$^{NTR}$ induced apoptosis characterized in that;
 this method does not require induction with p75$^{NTR}$ ligands such as for example NGF, LIF or neutrophins, and
 this method is applicable in a HTS screening format due to the transfection of cell suspensions that allows easy scale up and batch preparations to achieve a reproducible and homogenous transfection efficacy throughout the multi-well microplates.

It is accordingly a first aspect of the present invention to provide a method to identify a test compounds capability to modulate p75$^{NTR}$ induced apoptosis, said method comprising:
 i. transfecting a suspension of eukaryotic cells with a vector encoding p75$^{NTR}$ or a cell death inducing fragment thereof,
 ii. contacting said cells with the compound to be tested, and
 iii. determine the apoptotic response in said cells, wherein an alteration in apoptotic response in the presence of said test compound compared to the apoptotic response in the absence of the test compound is an indication of the ability of the test compound to modulate p75$^{NTR}$ induced apoptosis.

In this method according to the invention the suspension of eukaryotic cells is selected from the group consisting of CHO cells, human neuroblastoma SK-N-BE cells, human neuroblastoma SH-SY-5Y cells, sensory dorsal root ganglial neurons, Schwann cells, human melanoma cell line A875, rat PC12 cells and Hek293T cells, in particular Hek293T cells. The cell suspensions are used at a cell density of 0.4-3.0×10$^4$ cells/100 µl. In particular in a range of 0.5-2.0×10$^4$ cells/100 µl, even more particularly in a range of 0.4-0.8×10$^4$ cells/100 µl. In a further embodiment of the present invention said cells are transfected in the presence of a lipid-based transfection reagent, in particular at ratio of transfection reagent to DNA of 6-1, even more particular in a ratio of transfection reagent to DNA of 5-3, most particular at a ratio of 4. Expressed per 10 ml of final transfection mix the amount of transfection reagent is in a range of 8.0-12.0 µl, in particular in a range of 6.0-10.0 µl, more particular 10.0 µl and the amount of DNA is in a range of 2.0-3.5 µg, in particular 2.0-3.0, more particular 2.5 µl.

The lipid-based transfection reagents typically used are the commercially available reagentia such as for example Lipofectamine, Effectene and DMRIE-C. As exemplified hereinafter, in a preferred embodiment the tranfection is performed with a suspension of Hek293T cells at a density of 5000 cells/100 µl using lipofectamine as transfection reagent at a ratio of transfection reagent to DNA of 4.

The apoptotic response of the cells in the method according to the invention is determined using art known procedures. In particular using annexin V or nuclear staining. In a preferred embodiment the apoptotic response is determined using Annexin-V-Alexa Fluor 488 and Hoechst 33342.

The p75$^{NTR}$ receptor as used hereinbefore corresponds to the rat p75$^{NTR}$ receptor (SEQ ID No.2) or the mammalian orthologs thereof. The p75$^{NTR}$ cell death inducing fragment as used hereinbefore comprises the p75 Chopper domain (SEQ ID No.10) and in particular consists of p75_ICD (SEQ ID No.4), p75_CD (SEQ ID No.6) or p75_TNF (SEQ ID No.8).

This and further aspects of the present invention will be discussed in more detail hereinafter.

DETAILED DESCRIPTION

Figure 1:
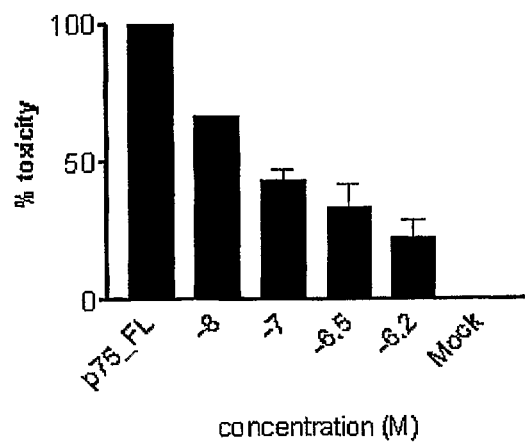
FIG. 1: Dose response curve of a test compound on the apoptotic response of Hek293 cells transfected with the rat p75$^{NTR}$ construct (SEQ ID No.:1). The induced toxicity being quantified by annexin V staining and expressed as relative differences between the p75$^{NTR}$ induced toxicity and control (mock), taking the relative toxicity of p75_FL as 100%. The assay was performed at 384 well plate format with quantification as percentage of annexin V-Alexa-488 positive cells, counter staining by Hoechst 33342.
Figure 2:
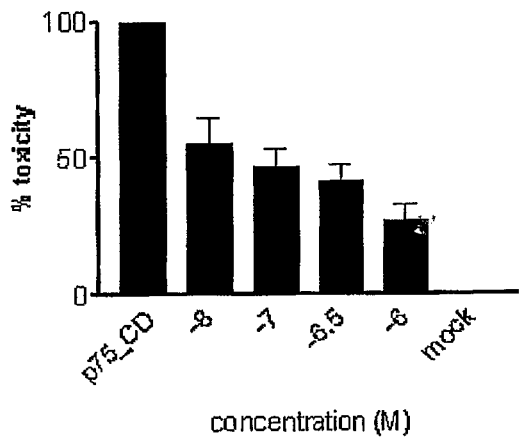
FIG. 2: Dose response curve of a test compound on the apoptotic response of Hek293 cells transfected with the rat p75$^{NTR}$ chopper construct (SEQ ID No.:5). The induced toxicity being quantified by annexin V staining and expressed as relative differences between the p75$^{NTR}$ induced toxicity and control (mock), taking the relative toxicity of p75_CD as 100%. The assay was performed at 96 well plate format with quantification as average annexin V-Alexa-488 fluorescence intensity, counter staining by Hoechst 33342.

For the purposes of describing the present invention: the p75$^{NTR}$ receptor as used herein refers to the rat NGFR receptor protein, also known as low-affinity nerve growth factor receptor, Gp80-LNGFR, p75 ICD and p75$^{NTR}$, characterized in Radeke et al., Nature 1987, 325, 593-597, and available at Swiss-Prot Accession No. P07174, as well as to its mammalian orthologs which are at least 70% identical, preferably 80% identical, even more preferably at least 90% identical, preferably at least 95% identical to, more preferably at least 97% identical to, and most preferably at least 99% identical to SEQ ID No.: 2, in particular said mammalian ortholog consists of the human p75$^{NTR}$ receptor (Swiss-Prot: P08138—SEQ ID No.: 11), the mouse p75$^{NTR}$ receptor (Swiss-Prot: Q920W1—SEQ ID No.: 12) or the chick p75$^{NTR}$ receptor (Swiss-Prot: P18519—SEQ ID No.:13).

Instead of the full-length p75$^{NTR}$ receptor a "cell death inducing" fragment of said receptor can be used in the assays of the invention. Said cell death inducing fragments correspond to deletion constructs of the p75$^{NTR}$ receptor protein that retain the capability to induce apoptosis in a cell, such as for example the truncated p75$^{NTR}$ proteins sptc152 and sptc35 described in Coulson et al. (2000, J. Biol. Chem. 275, 30537-30545). Further deletion constructs consist of: a construct that encodes the p75$^{NTR}$ signal peptide linked to the trans-membrane region and the entire intra-cellular domain of the p75$^{NTR}$ protein, in particular encoding the amino acids corresponding to amino acids 1 to 32 linked to amino acids 247 to 425 of the rat p75$^{NTR}$ protein (SEQ ID No.4);—a construct that encodes the p75$^{NTR}$ signal peptide linked to the transmembrane region and the intra-cellular juxta-membrane region of the p75$^{NTR}$ protein, in particular encoding the amino acids corresponding to amino acids 1 to 32 linked to amino acids 247 to 308 of the rat p75$^{NTR}$ protein (SEQ ID No.6);—a construct that encodes a protein consisting of the signal-peptide, trans-membrane region and part of the intra-cellular domain which lacks the "chopper" domain but includes the TNF receptor like death domain, in particular encoding the amino acids corresponding to amino acids 1 to 32, linked to amino acids 247-273 and amino acids 303 to 425 of the rat p75$^{NTR}$ protein (SEQ ID No.8). In one embodiment the p75$^{NTR}$ cell death inducing fragments are selected from polypeptides having at least 70%, 80%, 90%, 95%, 97% or 99% sequence identity with the Chopper domain (SEQ ID no.: 10), p75_ICD (SEQ ID NO.: 4), p75_CD (SEQ ID No.: 6) or p75_NTF (SEQ ID No.: 8). In a preferred embodiment of the present invention the p75$^{NTR}$ cell death inducing fragment as used hereinbefore comprises the p75 Chopper domain (SEQ ID No.10) and in particular consists of p75_ICD (SEQ ID No.4), p75_CD (SEQ ID No.6) or p75_NTF (SEQ ID No.8).

Methods for comparing the identity and similarity of two or more sequences are well known in the art. Thus for instance, programs available in the Wisconsin Sequence Analysis Package, version 9.1 (Devreux J. et al, Nucleic Acid Res., 12, 387-395, 1984), for example the programs BESTFIT and GAP, may be used to determine the % identity between two polynucleotides and the % identity and the % similarity between two peptide or polypeptide sequences. BESTFIT uses the "local homology" algorithm of Smith and Waterman (J. Mol. Biol., 147, 195-197, 1981) and finds the best single region of similarity between two sequences. BESTFIT is more suited to compare two polynucleotide or two peptide or polypeptide sequences that are dissimilar in length, the program assuming that the shorter sequence represents a portion of the longer. In comparison, GAP aligns two sequences, finding a "maximum similarity", according to the algorithm of Needleman and Wunsch (J. Mol. Biol., 48, 443-453, 1970). GAP is more suited to compare sequences that are approximately the same length and an alignment is expected over the entire length. Preferably, the parameters "Gap Weight" and "Length Weight" used in each program are 50 and 3, for polynucleotide sequences and 12 and 4 for polypeptide sequences, respectively. Preferably, % identities and similarities are determined when the two sequences being compared are optimally aligned. Other programs for determining identity and/or similarity between sequences are also known in the art, for instance the BLAST family of programs (Altschul S F et al, Nucleic Acids Res., 25:3389-3402, 1997).

The term "compound", "test compound", "agent" or "candidate agent" as used herein can be any type of molecule, including for example, a peptide, a polynucleotide, or a small molecule that one wishes to examine for their capability to modulate p75$^{NTR}$ induced apoptosis, and wherein said agent may provide a therapeutic advantage to the subject receiving it. The candidate agents can be administered to an individual by various routes, including, for example, orally or parenterally, such as intravenously, intramuscularly, subcutaneously, intraorbitally, intracapsularly, intraperitoneally, intrarectally, intracisternally or by passive or facilitated absorption through the skin, using for example a skin patch or transdermal iontophoresis, respectively. Furthermore the compound can be administered by injection, intubation or topically, the latter of which can be passive, for example, by direct application of an ointment, or active, for example, using a nasal spray or inhalant, in which case one component of the composition is an appropriate propellant. The route of administration of the compound will depend, in part, on the chemical structure of the compound. Peptides and polynucleotides, for example, are not particular useful when administered orally because they can be degraded in the digestive tract. However, methods for chemically modifying peptides, for example rendering them less susceptible to degradation are well know and include for example, the use of D-amino acids, the use of domains based on peptidomimetics, or the use of a peptoid such as a vinylogous peptoid.

The agent used in the screening method may be used in a pharmaceutically acceptable carrier. See, e.g., *Remington's Pharmaceutical Sciences*, latest edition, by E.W. Martin Mack Pub. Co., Easton, Pa., which discloses typical carriers and conventional methods of preparing pharmaceutical compositions that may be used in conjunction with the preparation of formulations of the agents and which is incorporated by reference herein.

Cells

As already outlined above, the present invention provides a suspension of cells transiently transfected with a vector encoding p75$^{NTR}$ or a death inducing fragment thereof. In particular HEK 293T cells transfected with said vectors. HEK 293T cells (ATCC accession number CRL-1573) are derived from transformed embryonal human kidney cells and known to have adherent growth properties (Graham F. L., et al. 1977, J. Gen. Virol. 36:59-72). HEK 293 cells have a normal inclination to form aggregates which affect cell viability when kept in suspension (David A. E. et al., 1999 Focus 21(1):22-24). As a consequence transfection of HEK293 cells is typically performed on adhered cells. In a multi-well screening format this implies that the cells are plated in each individual well at least one day before transfection. Using the transfection protocol of the present invention, a homogenous transfection mixture is added to a suspension of HEK293 cells and the thus obtained cell mixture is plated to the individual cells. Compared to the above, this not only reduces the cycle time, but also the number of pipeting steps and as such provides a more homogenous, reproducible assay format. In addition, given the particular transfection method of the present invention, only small numbers of cells, DNA and transfection reagent are required, further reducing the cost per well.

The vectors used in the methods according to the invention are routinely constructed in the art of molecular biology and may involve the use of plasmid DNA and appropriate initiators, promoters, enhancers and other elements, which may be necessary, and which are positioned in the correct orientation, in order to allow for protein expression. Generally, any system or vector suitable to maintain, propagate or express polynucleotides to produce a polypeptide in a host may be used. The appropriate nucleotide sequence, i.e. the polynucleotide sequences encoding either the p75$^{NTR}$ protein or a death inducing fragment thereof as defined hereinbefore, may be inserted into an expression system by any of a variety of well-known and routine techniques such as for example those set forth in Current Protocols in Molecular Biology, Ausbel et al. eds., John Wiley & Sons, 1997.

It is thus an object of the present invention to provide vectors encoding p75$^{NTR}$ or death inducing fragments thereof, wherein said vectors comprise the polynucleotide sequences selected from the polynucleotide sequences having at least 70%, 80%, 90%, 95%, 97%, or 99% sequence identity with SEQ ID No.: 1 (Rat p75$^{NTR}$), SEQ ID No.: 3 (p75$^{NTR}$_ICD), SEQ ID No.: 5 (p75$^{NTR}$_CD) or SEQ ID No.: 7 (p75$^{NTR}$_TNF).

In a particular embodiment the HEK293 cells according to the invention are transfected with the commercially available expression vectors pcDNA3.1 comprising the polynucleotide sequences encoding for rat p75$^{NTR}$ (SEQ ID No.:1) or the death inducing fragments thereof consisting of p75$^{NTR}$_ICD (SEQ ID No.: 3), p75$^{NTR}$_CD (SEQ ID No.:5) and p75$^{NTR}$_TNF (SEQ ID No.:7) respectively.

For further details in relation to the preparation of nucleic acid constructs, mutagenesis, sequencing, introduction of DNA into cells and gene expression, and analysis of proteins, see for example, Molecular Cloning: a Laboratory Manual: 2nd edition, Sambrook et al., 1989, Cold Spring Harbor Laboratory Press.

Assays

The present invention also provides an assay to identify a compounds capability to modulate p75$^{NTR}$ induced apoptosis in a cell.

Assays of the present invention can be designed in many formats generally known in the art of screening compounds for their capability to modulate an apoptotic response in a cell. Apoptosis in a cell is typically determined based on morphological and biochemical criteria. Morphological characteristics include for example, cell shrinkage, cytoplasmic condensation, chromatin segregation, nuclear condensation, membrane bledding and the formation of membrane-bound apoptotic bodies. Traditional methods to determine these morphological changes include light and electron microscopy using amongst others vital dyes and nuclear stains such as for example DAPI, DRAQ-5, SYBR14, propidium iodine, Hoechst staining. Biochemical changes are associated with the activation of a cell death related pathways, such as for example MAP kinase activation, calpain activation and caspase-3 activation, which ultimately result in internucleosomal DNA cleavage into oligonucleosome-length fragments. The commonly used biochemical methods include DNA laddering, Annexin binding, assessing mitochondrial transmembrane potential loss and measuring enzyme activity in one or more of the cell death related pathways such as for example phosphorylation of c-Jun (JNK), PARP cleavage and Cytochrome C release. (Budd R. C., et al. 1997, Coron Artery Dis. 8(10): 593-597; Loo D. T. and Rillema J. R., 1998, Methods Cell Biol. 57:251-264)

The assays of the present invention advantageously exploit the fact that the transfection of a suspension of cells with p75$^{NTR}$ or a cell death inducing fragment of said p75$^{NTR}$ no longer requires the presence of a p75$^{NTR}$ ligand in the cultivation medium to induce apotosis in said cells and accordingly simplifies the method to determine the capability of a compound to modulate p75$^{NTR}$ induced apoptosis in a cell.

Therefore, the present invention provides an assay for screening test compounds, the assay comprising a) transfecting a suspension of cells with p75$^{NTR}$ or a death inducing fragment thereof; b) incubating said cells with the compounds to be tested; and c) measure the apoptotic response of said cells.

In a first embodiment of this invention the suspension of cells is selected from the group consisting of CHO cells, human neuroblastoma SK-N-BE cells, human neuroblastoma SH-SY-5Y cells, sensory dorsal root ganglial neurons, Schwann cells, human melanoma cell line A875, rat PC12 cells and Hek293T cells. Said cells are transfected with the vectors according to the invention (see supra) using art-known transfection procedures, in particular using lipid-based transfection reagentia such as for example Lipofectamine, Effectene and DMRIE-C.

In a particular embodiment of this invention the suspension of cells consist of HEK293T cells transfected with a vector according to the invention using Lipofectamine as transfection reagent.

Methods to measure the apoptotic response in the cells are provided hereinbefore and typically comprise the use of an early apoptotic marker such as for example detectably labeled Annexin V in combination with nuclear stains such as for example Hoechst 33342, DAPI and DRAQ-5. Detectably labeled Annexin-V include radiolabeled, fluorescently labeled, and enzymaticaly labeled Annexin V such as for example the commercially available the fluorescently labeled Annexin-V-Alexa fluor 350, Annexin-V-Alexa fluor 488, Annexin-V-Alexa fluor 568, Annexin-V-Alexa fluor 594, Annexin-V-Alexa fluor 647, Annexin-V-FITC and the enzymatically labeled Annexin-V-Biotin, Annexin-V-Cy5 and Annexin-V-Cy5.5

In another embodiment of this invention the apoptotic response of the cells is determined using the combination of Hoechst staining, to determine to total number of cells, with Annexin binding, to determine the fraction of apoptotic cells. In a particular embodiment the apoptotic response is determined using Hoechst 33342 and Annexin-V-Alexa fluor 488.

Method of Treatment

A preferred use of the compounds identified using the methods of the present invention is in the treatment of vascular pathologies such as for example atherosclerosis, congenital and rheumatic heart disease and vascular inflammation and in the treatment of pathologies associated with neuronal development and neuronal apoptosis. The latter include the major diseases in CNS such as stroke, Parkinson's disease, Huntington's disease, Alzheimer's disease, ALS, SCI, MS MND and prion diseases, i.e TSE.

Another preferred use of the compounds identified using the methods of the present invention is in the production of other therapeutic effects, such as analgesic effects. The compounds identified using the methods of the present invention are preferably used to produce one or more of these effects in a patient in need of such treatment.

Patients in need of such treatment can be identified by standard medical techniques. For example, the production of analgesic activity can be used to treat patients suffering from clinical conditions of acute and chronic pain including the following: peripheral neuropathies such as occur with diabetes mellitus and multiple sclerosis; central pain such as that seen with spinal cord lesions; hyperalgesia; cancer pain and allodynia.

In a method of treating a patient, a therapeutically effective amount of a compound that in vitro modulates $p75^{NTR}$ induced apoptosis, is administered to the patient. In particular the systemic or topical administration of an effective amount of a compound according to the invention, to warm-blooded animals, is including humans. Typically, the compound modulates $p75^{NTR}$ receptor activity by acting as an allosteric modulator or as an agonist or antagonist of p75 binding site activation. Preferably, the patient has a neurological disease or a disorder, preferably the compound has an effect on a physiological activity. Such physiological activity can be convulsions, neuroprotection, neuronal death, neuronal development, central control of cardiac activity, waking, control of movements and control of vestibo ocular reflex.

Diseases or disorders which can be treated by modulating $p75^{NTR}$ induced apoptosis include one or more of the following types: (1) those characterized by abnormal $p75^{NTR}$ expression (e.g. different in kind (mutants) or magnitude); (2) those characterized by an abnormal amount of an extracellular or intracellular messenger that activates the $p75^{NTR}$ receptor; (3) those characterized by an abnormal effect (e.g., a different effect in kind or magnitude) of an intracellular or extracellular messenger which can itself be ameliorated by $p75^{NTR}$ receptor activity; and (4) other diseases or disorders in which modulation of $p75^{NTR}$ receptor activity will exert a beneficial effect, for example, in diseases or disorders where the production of an intracellular or extracellular messenger stimulated by $p75^{NTR}$ activity compensates for an abnormal amount of a different messenger.

The compounds and methods can also be used to produce other effects such as an analgesic effect, cognition-enhancement effect, and a muscle-relaxant effect.

A "patient" refers to a mammal in which modulation of a $p75^{NTR}$ receptor activity will have a beneficial effect. Patients in need of treatment involving modulation of $p75^{NTR}$ receptor activity can be identified using standard techniques known to those in the medical profession. Preferably, a patient is a human having a disease or disorder characterized by one more of the following: characterized by abnormal $p75^{NTR}$ expression (e.g. different in kind (mutants) or magnitude); (2) those characterized by an abnormal amount of an extracellular or intracellular messenger that activates the $p75^{NTR}$ receptor; (3) those characterized by an abnormal effect (e.g., a different effect in kind or magnitude) of an intracellular or extracellular messenger which can itself be ameliorated by $p75^{NTR}$ receptor activity.

By "therapeutically effective amount" is meant an amount of an agent which relieves to some extent one or more symptoms of the disease or disorder in the patient; or returns to normal either partially or completely one or more physiological or biochemical parameters associated with or causative of the disease.

More generally, this invention provides a method for modulating metabotropic glutamate receptor activity by providing to a cell having a metabotropic glutamate receptor an amount of a metabotropic glutamate receptor modulating molecule sufficient to either mimic one or more effects of glutamate at the metabotropic glutamate receptor, or block one or more effects of glutamate at the metabotropic glutamate receptor. The method can carried out in vitro or in vivo.

Such agents may be formulated into compositions comprising an agent together with a pharmaceutically acceptable carrier or diluent. The agent may in the form of a physiologically functional derivative, such as an ester or a salt, such as an acid addition salt or basic metal salt, or an N or S oxide. Compositions may be formulated for any suitable route and means of administration. Pharmaceutically acceptable carriers or diluents include those used in formulations suitable for oral, rectal, nasal, inhalable, topical (including buccal and sublingual), vaginal or parenteral (including subcutaneous, intramuscular, intravenous, intradermal, intrathecal and epidural) administration. The choice of carrier or diluent will of course depend on the proposed route of administration, which, may depend on the agent and its therapeutic purpose. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For solid compositions, conventional non-toxic solid carriers include, for example, pharmaceutical grades of mannitol, lactose, cellulose, cellulose derivatives, starch, magnesium stearate, sodium saccharin, talcum, glucose, sucrose, magnesium carbonate, and the like may be used. The active compound as defined above may be formulated as suppositories using, for example, polyalkylene glycols, acetylated triglycerides and the like, as the carrier. Liquid pharmaceutically administrable compositions can, for example, be prepared by dissolving, dispersing, etc, an active compound as defined above and optional pharmaceutical adjuvants in a carrier, such as, for example, water, saline aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see Gennaro et al., Remington's Pharmaceutical Sciences, Mack Publishing Company, Easton, Pa., 18th Edition, 1990.

The composition or formulation to be administered will, in any event, contain a quantity of the active compound(s) in an amount effective to alleviate the symptoms of the subject being treated.

Dosage forms or compositions containing active ingredient in the range of 0.25 to 95% with the balance made up from non-toxic carrier may be prepared.

For oral administration, a pharmaceutically acceptable non-toxic composition is formed by the incorporation of any of the normally employed excipients, such as, for example, pharmaceutical grades of mannitol, lactose, cellulose, cellulose derivatives, sodium crosscarmellose, starch, magnesium stearate, sodium saccharin, talcum, glucose, sucrose, magnesium, carbonate, and the like. Such compositions take the form of solutions, suspensions, tablets, pills, capsules, powders, sustained release formulations and the like. Such compositions may contain 1%-95% active ingredient, more preferably 2-50%, most preferably 5-8%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, triethanolamine sodium acetate, etc.

The percentage of active compound contained in such parental compositions is highly dependent on the specific nature thereof, as well as the activity of the compound and the needs of the subject. However, percentages of active ingredient of 0.1% to 10% in solution are employable, and will be higher if the composition is a solid which will be subsequently diluted to the above percentages. Preferably, the composition will comprise 0.2-2% of the active agent in solution.

Throughout this description the terms "standard methods", "standard protocols" and "standard procedures", when used in the context of molecular biology techniques, are to be understood as protocols and procedures found in an ordinary laboratory manual such as: Current Protocols in Molecular Biology, editors F. Ausubel et al., John Wiley and Sons, Inc. 1994, or Sambrook, J. Fritsch, E. F. and Maniatis, T. Molecular Cloning: A laboratory manual, 2nd Ed., Cold Spring Harbor Laboratory Press, Cold Spring Harbor, N.Y. 1989.

This invention will be better understood by reference to the Experimental Details that follow, but those skilled in the art will readily appreciate that these are only illustrative of the invention as described more fully in the claims that follow thereafter. Additionally, throughout this application, various publications are cited. The disclosure of these publications is hereby incorporated by reference into this application to describe more fully the state of the art to which this invention pertains.

Experimental
Material and Methods
p75$^{(NTR)}$ Constructs

A pCDNA3 construct (p75_FL), containing the wild type rat p75$^{(NTR)}$ cDNA sequence (SEQ ID No.1), according EMBL accession number X05137 was kindly provided by Carlos Ibanez. Two deletion constructs encoding previously described, truncated forms of the p75$^{(NTR)}$ receptor (Coulson et al., 2000) were generated by Polymerase Chain Reaction (PCR). Both deletion constructs: p75_Intra-Cellular Domain (p75_ICD) (SEQ ID No.3) and p75 Chopper Domain (p75_CD) (SEQ ID No.5) were generated by cloning the PCR products into the multi-cloning site of pCDNA3 vector using introduced 5' Eco RI and 3' ApaI restriction sites. The 114 nucleic acid 5' untranslated region (UTR) and the 163 nucleic acid 3'UTR present in the p75_FL construct, were maintained in the deletion constructs.

The p75_ICD DNA construct encodes amino acids 1 to 32 linked to amino acids 247 to 425 of the rat p75$^{(NTR)}$ protein. Hence including the signal peptide, trans-membrane region and the entire intra-cellular domain.

The p75_CD DNA construct encodes amino acids 1 to 32 linked to amino acids 247 to 308. Hence including the signal peptide, trans-membrane region and the intra-cellular juxtamembrane region, designated "chopper" death domain.

The p75_NTF DNA construct encodes a polypeptide consisting of amino acids 1 to 32 linked to amino acids 247 to 273 and amino acids 303 to 425 of the rat p75$^{(NTR)}$ protein. Hence including the signal peptide, trans-membrane region and part of the intra-cellular domain lacking the Chopper domain but including the TNF receptor like death domain. Between the signal peptide and the trans-membrane region, the human influenza hemmagglutinin protein (HA) epitope tag was inserted.

The Assay

All cell culture and incubation steps were performed in Dulbecco's Modified Eagle Medium (DMEM) (Invitrogen Corporation) supplemented with either 10% or 3% Fetal Bovine Serum (FBS) at 37° C. and 5% $CO_2$, unless indicated otherwise.

Preparation:

On day one, HEK293T cells were seeded in p175 cm$^2$ culture flasks at a density of 60.000 cells/cm$^2$ and left to grow overnight (DMEM+10% FBS) until 40-70% confluency was reached.

Transfection:

On day two, the overnight grown, HEK293T cells were transferred to 96 well plates, each well containing 5000 cells in 100 μl medium (DMEM+3% FBS) and transfected for 48 hours, using a for this assay developed method, Briefly:

To ensure reproducibility, enough transfection mix was prepared for at least 250 wells. When larger number of wells were required, volumes and amounts were scaled up proportionally.

The transfection mix for 250 wells was prepared as follows:

To a tube containing DMEM without serum, 6.25 μg of the appropriate DNA construct was added to a final volume of 1250 μl and vortexed. To a second tube containing 1225 μl DMEM without serum, 25 μl Lipofectamine2000 (Invitrogen Corporation) was added and vortexed. After a five minute incubation period at Room Temperature (RT), the contents of the two tubes was combined, mixed gently and incubated for a further 20 minutes at RT.

Meanwhile HEK293T cells were dislodged from the p175 cm$^2$ culture flasks using 2 ml of a 0.005% Trypsin, 0.04% EDTA solution, followed by trypsin neutralization with 8 ml medium (DMEM+3% FBS). The cell concentration was determined using a Coulter counter and adjusted to 55.000 cells/ml with medium (DMEM+3% FBS). At the end of the 20 minutes incubation period, 25 ml transfection suspension was prepared by combining the DNA/lipofectamine2000 mix with 22.5 ml cell suspension. After gentle but thorough mixing, 100 μl of the transfection suspension was transferred immediately to the appropriate wells of a poly-L-lysine coated 96 well plate. Ultimately each plate containing separate wells, holding cells transfected with empty pCDNA3 vector (mock transfection, negative control), pCDNA3_ICD, pcDNA3_TNF and/or pCDNA3_CD DNA construct.

The plates were incubated for 48 hours before measurement.

Addition of Compounds:

To determine the influence of a number of small molecules on the apoptosis induced by the above mentioned DNA expression constructs, additions were made to appropriate wells of the 96 well plates, six hours after the start of the transfection. Compounds were added as a 10 times stock solution in medium (DMEM+3% FBS+1% DMSO), resulting in a final volume of 110 ul medium per well and a DMSO concentration of about 0.1%. Wells without compound addition were adjusted to the same volume and DMSO concentration.

Detection:

One hour before detection, Annexin-V-Alexa Fluor 488 conjugate (Molecular probes) and Hoechst 33342 (Molecular probes) were added to each well at final dilution of 50 times and concentration of 6.7 μg/ml respectively. Subsequently, plates were incubated for an additional hour.

Quantification of total cell number (Hoechst positive), apoptotic plus necrotic cell number and fluorescence intensity (Annexin V positive) was achieved by analyzing the 96 well plates on the MIAS-1 or MIAS-2 cellular imaging platform (Union Biometrica).

Coulson E. J., *JBC* "Chopper, a new death domain of p75 neurotrophin receptor that mediates neuronal cell death", 2000, 275 (9), 30537-30545.

What is claimed is:

1. A method to identify a test compound which modulates apoptosis induced by p75$^{NTR}$, said method comprising:
   i. transfecting a suspension of eukaryotic cells with a vector encoding a p75$^{NTR}$ polypeptide comprising SEQ ID NO:4 or SEQ ID NO:6;
   ii. contacting said cells with said test compound; and
   iii. determining the apoptosis in said cells, wherein an alteration in the apoptosis in the presence of said test compound compared to the apoptosis in the absence of the test compound is an indication said test compound modulates apoptosis induced by the p75$^{NTR}$ polypeptide.

2. The method according to claim 1 wherein the suspension of eukaryotic cells is selected from the group consisting of CHO cells, human neuroblastoma SK-N-BE cells, human neuroblastoma SH-SY-5Y cells, sensory dorsal root ganglial neurons, Schwann cells, human melanoma cell line A875, rat PC12 cells and Hek293T cells.

3. The method according to claim 2, wherein the suspension of eukaryotic cells comprises HEK293 cells.

4. The method according to claim 2, wherein the suspension of eukaryotic cells comprises HEK293T cells.

5. The method according to claim 1 wherein apoptosis is determined by observing morphological and/or biochemical changes selected from the group consisting of cell shrinkage, cytoplasmic condensation, chromatin segregation, nuclear condensation, membrane blebbing, formation of membrane-bound apoptotic bodies, DNA laddering, Annexin binding and loss of mitochondrial membrane potential.

6. The method according to claim 1 wherein apoptosis is determined by observing morphological and/or biochemical changes selected from annexin V binding and nuclear staining.

7. The method according to claim 6 wherein the annexin V is fluorescently labeled.

8. The method according to claim 1 wherein the suspension of eukaryotic cells is transfected in the presence of a lipid-based transfectin reagent.

9. The method according to claim 8, wherein the suspension of eukaryotic cells has a cell density in a range of 0.4-3.0×10$^4$ cells/100 µl.

10. The method according to claim 8 wherein the lipid-based transfection reagent is selected from the group consisting of Lipofectamine, DMRIE-C and Effectene.

11. The method according to claim 1, wherein the p75$^{NTR}$ polypeptide comprises SEQ ID NO: 4.

12. The method according to claim 1, wherein the p75$^{NTR}$ polypeptide comprises SEQ ID NO: 6.

* * * * *